(12) United States Patent  
Toth et al.

(10) Patent No.: US 8,357,894 B2
(45) Date of Patent: Jan. 22, 2013

(54) MICROCALORIMETRY FOR X-RAY SPECTROSCOPY

(75) Inventors: Milos Toth, Portland, OR (US); Michael R. Scheinfein, Portland, OR (US); Eric Silver, Needham, MA (US); David Narum, Banks, OR (US)

(73) Assignee: FEI Company, Hillsboro, OR (US)

( * ) Notice: Subject to any disclaimer, the term of this patent is extended or adjusted under 35 U.S.C. 154(b) by 271 days.

(21) Appl. No.: 12/853,998

(22) Filed: Aug. 10, 2010

(65) Prior Publication Data

US 2011/0064191 A1 Mar. 17, 2011

Related U.S. Application Data

(60) Provisional application No. 61/232,779, filed on Aug. 10, 2009.

(51) Int. Cl.
*G21K 5/04* (2006.01)
(52) U.S. Cl. ........ 250/306; 250/307; 250/309; 250/310; 250/311; 250/396 R; 250/397; 378/70; 378/82; 378/84; 378/86
(58) Field of Classification Search .................. 250/305, 250/306, 307, 309, 310, 311, 396 R, 397; 378/70, 82, 84, 86
See application file for complete search history.

(56) References Cited

U.S. PATENT DOCUMENTS

| | | | |
|---|---|---|---|
| 5,389,792 A | 2/1995 | DiMarzio et al. | |
| 5,777,336 A | 7/1998 | Silver et al. | |
| 5,880,467 A | 3/1999 | Martinis et al. | |
| 6,094,471 A | 7/2000 | Silver et al. | |
| 6,310,350 B1 | 10/2001 | Silver et al. | |
| 6,479,818 B1 | 11/2002 | McCarthy et al. | |
| 6,594,337 B1 | 7/2003 | Silver et al. | |
| 7,232,487 B2 | 6/2007 | Silver et al. | |
| 2006/0198494 A1* | 9/2006 | Tanaka et al. | 378/45 |
| 2010/0148064 A1 | 6/2010 | Harrach et al. | |

OTHER PUBLICATIONS

Wollman et al., "High-resolution microcalorimeter energy-dispersive spectrometer for x-ray microanalysis and particle analysis", AIP Conference Proceedings 449 799 (1998).*
Bandler, Simon, et al., 'NTD-GE-based Microcalorimeter Performance,' Nuclear Instruments and Methods in Physics Research A, Apr. 1, 2000, pp. 273-277, vol. 444.
Sakamoto, Tetsue, et al., 'Development of a Ion and Electron Dual Focused Beam Apparatus for Three-Dimensional Microanalysis,' Jpn. J. Appl. Phys., Apr. 1, 1998, pp. 2051-2056, vol. 37.
Tanaka, Keiichi, et al., 'Transition Edge Sensor-Energy Dispersive Spectrometer (TED-EDS) and Its Applications,' IEICE Transactions on Electronics, Mar. 1, 2009, pp. 334-340, vol. E92-C, No. 3.
Wollman, D.A., et al., 'High-Resolution, Energy-Dispersive Microcalorimeter Spectrometer for X-Ray Microanalysis,' Journal of Microscopy, Dec. 1, 1997, pp. 196-223, vol. 188, No. 3.

(Continued)

*Primary Examiner* — David A Vanore
*Assistant Examiner* — Nicole Ippolito
(74) *Attorney, Agent, or Firm* — Scheinberg & Associates, PC; Michael G. Scheinberg

(57) ABSTRACT

An improved microcalorimeter-type energy dispersive x-ray spectrometer provides sufficient energy resolution and throughput for practical high spatial resolution x-ray mapping of a sample at low electron beam energies. When used with a dual beam system that provides the capability to etch a layer from the sample, the system can be used for three-dimensional x-ray mapping. A preferred system uses an x-ray optic having a wide-angle opening to increase the fraction of x-rays leaving the sample that impinge on the detector and multiple detectors to avoid pulse pile up.

21 Claims, 8 Drawing Sheets

OTHER PUBLICATIONS

Norrell, Johannes, et al., "High Resolution X-Ray Spectroscopy with a Microcalorimeter," U.S. Department of Energy Journal of Undergraduate Research, 2005, 5 pages, vol. V.

VeriCold Technologies, "Polaris Microcalorimeter EDS Detector," Feb. 2006, 2 pages, V. 1.4.

Semiconductor Equipment Assessment, "Project Synopsis: Microcalorimeter Type EDX System Assessment," Sep. 1, 2000, 2 pages.

Li, Qinghui, et al., "Spectral Analysis of Nanomaterials using a Transition-Edge Sensor Microcalorimeter Mounted on a Field-Emission Scanning Electron Microscope," Japanese Journal of Applied Physics, 2008, pp. 4835-4838, vol. 47, No. 6.

Nakai, Izumi, et al., "X-Ray Microanalysis of Biological Samples by High-Resolution Energy Dispersive Microcalorimeter Spectrometer Using a Low-Voltage Scanning Electron Microscope," Chemistry Letters, 2008, pp. 304-305, vol. 37, No. 3.

Kumakhov M. A. et al, "Multiple reflection from surface X-ray optics," Physics Reports, XX, XX, vol. 191, No. 5, Jan. 1, 1990, pp. 289-350, XP000560096.

F. Lasagni et al, "Nano-characterization of Cast Structures by FIB-Tomoography," Advanced Engineering Materials, vol. 10, No. 1-2, Feb. 1, 2008, pp. 62-66, XP55019498.

* cited by examiner

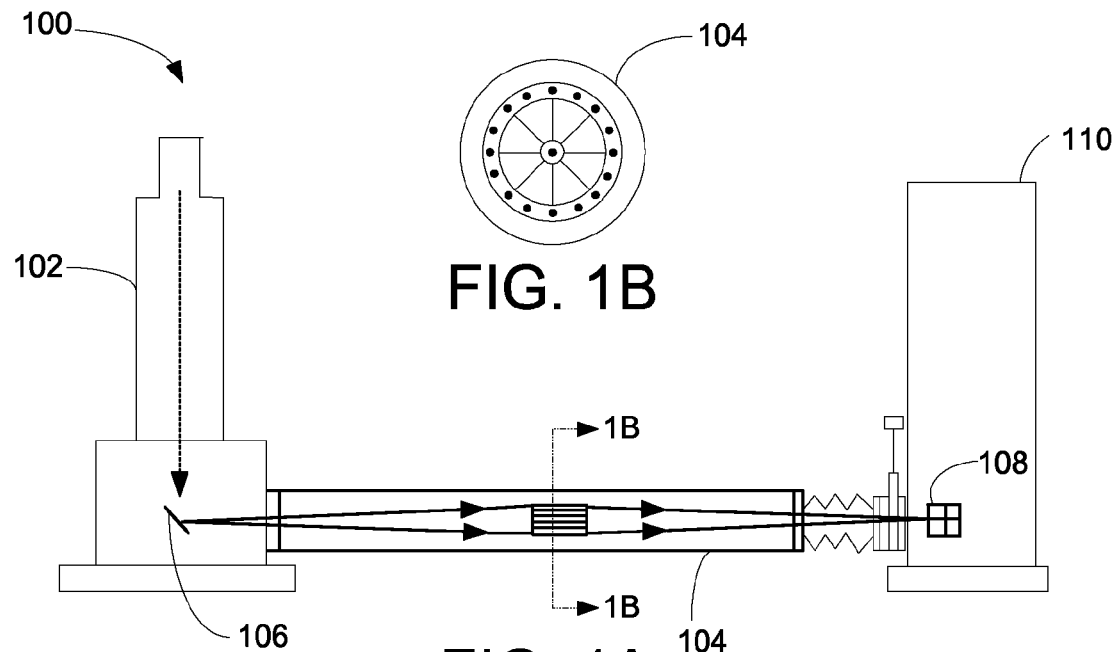
FIG. 1B
FIG. 1A
(Prior Art)
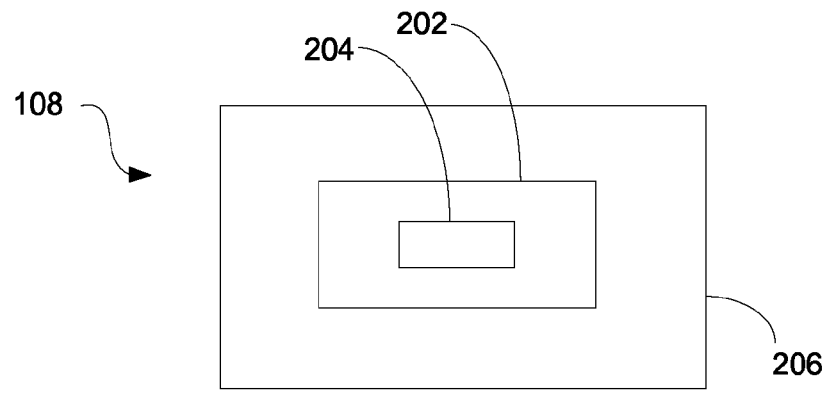
FIG. 2
(Prior Art)

Temperature
Response

MICROCALORIMETRY FOR X-RAY SPECTROSCOPY

This application claims priority from U.S. Prov. Pat. App. No. 61/232,779, filed Aug. 10, 2009, which is hereby incorporated by reference.

TECHNICAL FIELD OF THE INVENTION

The present invention relates to a system for determining the composition of a sample.

BACKGROUND OF THE INVENTION

Electron probe microanalyzers and electron microscopes having an attached x-ray spectrometer are used to determine the composition of microscopic or nanoscopic regions of a surface. The detectors determine the energy or wavelengths of x-rays emitted from the sample and infer the composition of material under the electron beam from the energy or wavelength of the x-rays. Because the x-rays characteristic of different materials may have energies that are only slightly different, a detector needs sufficient resolution to differentiate between closely spaced x-ray energies. To process a sample in reasonable amount of time, x-ray detectors need to be able to process a large number of x-rays each second. The number of x-rays that a detector can process each second is referred to as its "maximum count rate". The rate at which the received x-rays are processed is referred to as the "count rate" and is typically expressed in units of counts per second (cps).

Detectors that use a crystal to disperse and analyze x-rays of different wavelengths are referred to as wavelength dispersive spectrometers (WDS) and detectors that measure the energy of incoming x-rays are referred to as energy dispersive spectrometers (EDS). While a WDS can provide better spectral resolution and greater maximum count rate for a particular wavelength band of x-rays, an EDS is better adapted to measuring x-rays of different energies from multiple elements. Specifically, an EDS can acquire an entire spectrum in parallel, while a WDS is limited to serial acquisition. If two x-rays are received at nearly the same time in an EDS system, the energy measured by the detector will be the result of the both x-rays, and not accurately represent the sample material. Such an event is referred to as "pulse pileup." EDS detectors preferably process each x-ray quickly, so that each energy measurement is complete before the next x-ray is received.

The most common type of energy dispersive x-ray spectrometer uses a semiconductor x-ray detector in which the x-rays form electron-hole pairs. The electron-hole pairs are detected as an electric current and the number of pairs created by each x-ray depends on the energy of the x-ray. Although EDS systems with solid state detectors typically have a high count rate, up to hundreds of thousands of counts per second, their energy resolution at approximately 6 keV is worse than about 100 eV, which makes it impossible to differentiate closely spaced x-ray peaks.

Another type of energy dispersive x-ray spectrometer is the microcalorimeter-type EDS system, in which an x-ray is absorbed by a detector and the x-ray energy is determined by measuring an increase in temperature of the detector, the increase being proportional to the energy of the absorbed x-ray. The energy resolution of the microcalorimeter detector is superior to that of the semiconductor detector, less than 5 eV at an x-ray energy of approximately 6 keV in some systems, but microcalorimeter detectors typically are only capable of processing less than 500 x-rays per second. Microcalorimeter-type EDS systems are described, for example, in U.S. Pat. No. 5,880,467 to Martinis, et al. for "Microcalorimeter x-ray detectors with x-ray lens" and in Norrell and Anderson, "High Resolution X-Ray Spectroscopy with a Microcalorimeter," U.S. Department of Energy Journal of Undergraduate Research, Vol. 5, http://www.scied.science-.doe.gov/scied/JUR_v5/default.htm (2005).

FIG. 1A shows at typical microcalorimeter-type EDS system 100, which includes a scanning electron microscope 102 and an x-ray optic 104 that transmit x-rays emitted from a sample 106 to a detector 108 cooled by a cryostat 110. X-ray optics are typically either made from glass capillaries or from a thin metallic film, and are described, for example, in U.S. Pat. No. 6,094,471 to Silver et al. for "X-ray Diagnostic System," and U.S. Pat. No. 6,479,818 to McCarthy et al. for "Application of x-ray optics to energy dispersive spectroscopy." FIG. 1B shows an enlarged cross section of X-ray optic 104 of FIG. 1. X-ray optics used with a typical prior art microcalorimeter-type EDS has an acceptance angle of two to three degrees.

FIG. 2 shows that detector 108 typically comprises an x-ray absorber 202 and a temperature measuring device 204 in contact with the absorber. The x-ray absorber 202 and temperature measuring device 204 are maintained at a very low temperature, typically below 100 mK, have a very low combined heat capacity and a weak thermal link to a low temperature heat sink 206. The weak thermal link enables the thermal isolation needed for a temperature rise to occur. The output peak height (measured by the temperature measuring device) is related to the x-ray photon energy (E) & the combined heat capacity (C) of the absorber and the temperature measuring device. The energy resolution of the detector is approximately proportional to $(kT^2C)^{0.5}$ (where k is the Boltzmann constant and T is temperature). If the thermal link between the absorber and the low temperature heat sink is made weaker, the temperature of the absorber will rise further, increasing resolution. The weaker thermal link, however, increases the time required to cool the absorber after the x-ray is processed, thereby reducing the maximum count rate that can be processed by the detector.

The x-ray absorbing material is typically gold, and the temperature measuring device employed by most commercial systems includes a transition edge sensor, which includes a layer of non-superconducting material and a layer of superconducting material maintained near its transition temperature, that is, the temperature at which it stops superconducting. An electrical current through the transition edge sensor changes as the temperature of the sensor changes. The change in electrical current is typically amplified using a superconducting quantum interference device (SQUID).

The main technical advantage of microcalorimetry over solid state detectors is superior energy resolution. In the energy range of interest in typical microanalysis, prior art microcalorimeters have a resolution better than 15 eV, and in some cases better than 3 eV, whereas conventional EDS detectors are limited to a resolution of about 120 eV. Hence, microcalorimeters can resolve closely spaced characteristic x-ray lines. This is highly desirable for low voltage microanalysis, that is, microanalysis performed using an electron beam energy in the range of 1-5 keV, because:

The low energy end of the x-ray spectrum contains a large number of closely spaced characteristic x-ray peaks; specifically, the K, L and M lines of low, medium and high atomic number elements, respectively. For many materials, the low energy x-ray peaks overlap in conventional EDS spectra, necessitating the use of higher energy x-ray peaks which can only be excited by high energy (10-30 keV) electron beams.

In scanning electron microscopy, the electron penetration range and the electron-solid interaction volume are approximately proportional to $E_b^{1.67}$ and $(E_b^{1.67})^3$, respectively, where $E_b$ is the electron beam energy. X-rays are emitted from some fraction, typically the top one to two thirds of the interaction volume, the exact fraction being a function of the material type and the energy of the x-ray photons and the electron beam. Hence, the surface sensitivity and spatial resolution of microanalysis are strong functions of electron beam energy. Low beam energies are needed for maximum spatial resolution and surface sensitivity.

The main technical disadvantage of microcalorimetry over conventional EDS is low throughput, caused by two distinct phenomena. First, the solid angle over which x-rays are collected is severely limited by detector design requirements, causing the fraction of emitted x-rays collected by the detector to be very small. Specifically, the surface area of a typical x-ray absorber is on the order of 0.1 mm$^2$ and detector placement close to the sample is inhibited by the bulky nature of the hardware needed to cool the detector to below 100 mK. In contrast, solid state EDS detectors have surface areas in the range of 10 to 80 mm$^2$, and the detectors can be placed within a few centimeters of the sample. The second phenomenon that limits the throughput of microcalorimeter x-ray detectors is that the maximum count rate of a single detector is thermodynamically limited to less than approximately 500 cps. In contrast, the maximum count rates of conventional, solid state EDS (Si(Li) and silicon drift) detectors are on the order of $10^4$ to $10^5$ cps.

The low throughput of microcalorimeter-type EDS systems would require the use of a very high electron beam current to collect sufficient x-rays to form a useful x-ray map in a reasonable time period. A high electron beam current, however impedes electron beam focusing (due to the dependence of electron optical aberrations on beam current), causes rapid damage of electron sensitive samples, gives rise to rapid contamination buildup rates, and gives rise to severe charging of electrical insulators.

FIG. 3 shows portions of an x-ray spectrum of the mineral monazite drawn at three different scales. Enlarged graph 303 shows the large number of peaks available to characterize the sample in the low energy range. While the resolution is sufficiently high to differentiate a large number of closely spaced peaks, it took more than 11 hours to collect enough x-rays to analyze a single point on the sample.

For many applications, it is desired to create high resolution, two-dimensional or three-dimensional x-ray maps of the materials comprising a sample. That is, a region of a sample surface is divided into closely spaced points, and the material present in each point is determined by x-ray analysis, with points mapping to pixels on a display. This has not been possible using prior art microcalorimeter-type EDS systems; the design tradeoffs between high spatial resolution, high energy resolution, and high throughput, have prevented current microcalorimeter-type EDS systems from producing high resolution two or three-dimensional maps in a reasonable amount of time. For example, because the fraction of emitted x-rays that reach the detector is low, a high current electron beam is required to produce more x-rays. Increased beam current increases the size of the electron beam, reducing the spatial resolution of the material analysis at low electron beam energies. Moreover, the count rate of the microcalorimeter detector is limited. When the thermal path between the absorber and the cold substrate is sufficiently weak to provide a high amplitude temperature pulse upon absorption of an x-ray, the absorber takes longer to cool back down after a pulse is detected, reducing the count rate. A more thermally conductive path between the x-ray absorber and the cold sink substrate would allow more pulses per second to be counted, but would reduce the temperature change, and therefore the measurement accuracy of the x-ray energy.

The industry needs an EDS system capable x-ray mapping at high spatial resolution and high energy resolution.

SUMMARY OF THE INVENTION

An object of the invention, therefore, is to provide an EDS microcalorimeter system with the capability of performing high resolution mapping.

The present invention includes a microcalorimeter-type EDS system that provides sufficient resolution and throughput for practical high spatial resolution x-ray mapping of a sample. Some embodiments of the invention use a wide-angle opening for x-ray optics to increase the fraction of x-rays leaving the sample that impinge on the detector. Some embodiments of the invention use multiple detectors to improve the maximum count rate that can be processed by the EDS system. Some embodiments of the invention use a neutron transmutation doped temperature measurement element to improve resolution. Some embodiments use a tin x-ray absorber. Some embodiments of the invention use a JFET amplifier to measure the change in current of the temperature-sensing element.

Some embodiments of the invention include a dual beam system that provides an electron beam and an ion beam. The electron beam can be used to generate x-rays for analysis and the ion beam can be used to expose underlying material to analyze. By repeatedly analyzing a layer of material, removing the analyzed layer, and analyzing the newly uncovered layer, a three-dimensional map of material present on the sample can be created. Some embodiments use rapid electron beam scanning and periodic plasma cleaning to enable drift correction, and minimization of sample damage, contamination buildup and charging; that is problems the severity of which increases with improved spatial resolution.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more thorough understanding of the present invention, and advantages thereof, reference is now made to the following descriptions taken in conjunction with the accompanying drawings, in which:

FIG. 1 shows a typical prior art microcalorimeter-type energy dispersive x-ray spectrometer. FIG. 1B shows an enlarged cross section of the X-ray optic shown in FIG. 1A;

FIG. 2 shows a prior art detector used with the system of FIG. 1A;

The accompanying drawings are not intended to be drawn to scale. In the drawings, each identical or nearly identical component that is illustrated in various figures is represented by a like numeral. For purposes of clarity, not every component may be labeled in every drawing.

DETAILED DESCRIPTION OF PREFERRED EMBODIMENTS

Preferred embodiments of the present invention provide an improved microcalorimeter-type EDS system. Various embodiments of the system provide improved throughput, reliability, stability, and energy resolution.

A preferred method or apparatus of the present invention has many novel aspects, and because the invention can be embodied in different methods or apparatuses for different purposes, not every aspect need be present in every embodiment. Many the aspects of the described embodiments may be separately patentable.

Figure 3:
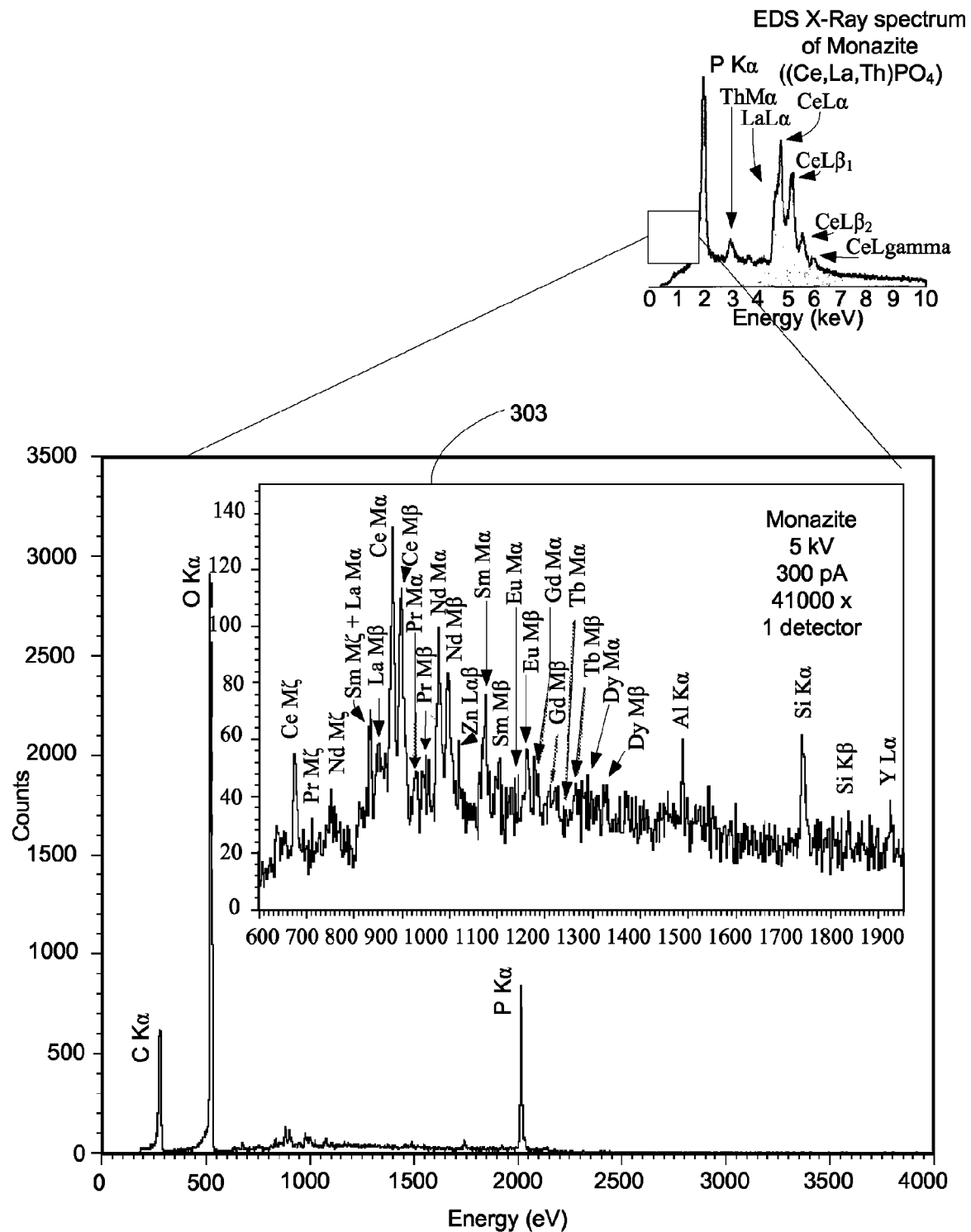
FIG. 3 shows portions of an x-ray spectrum drawn at three different scales of the mineral monazite.
Figure 4:
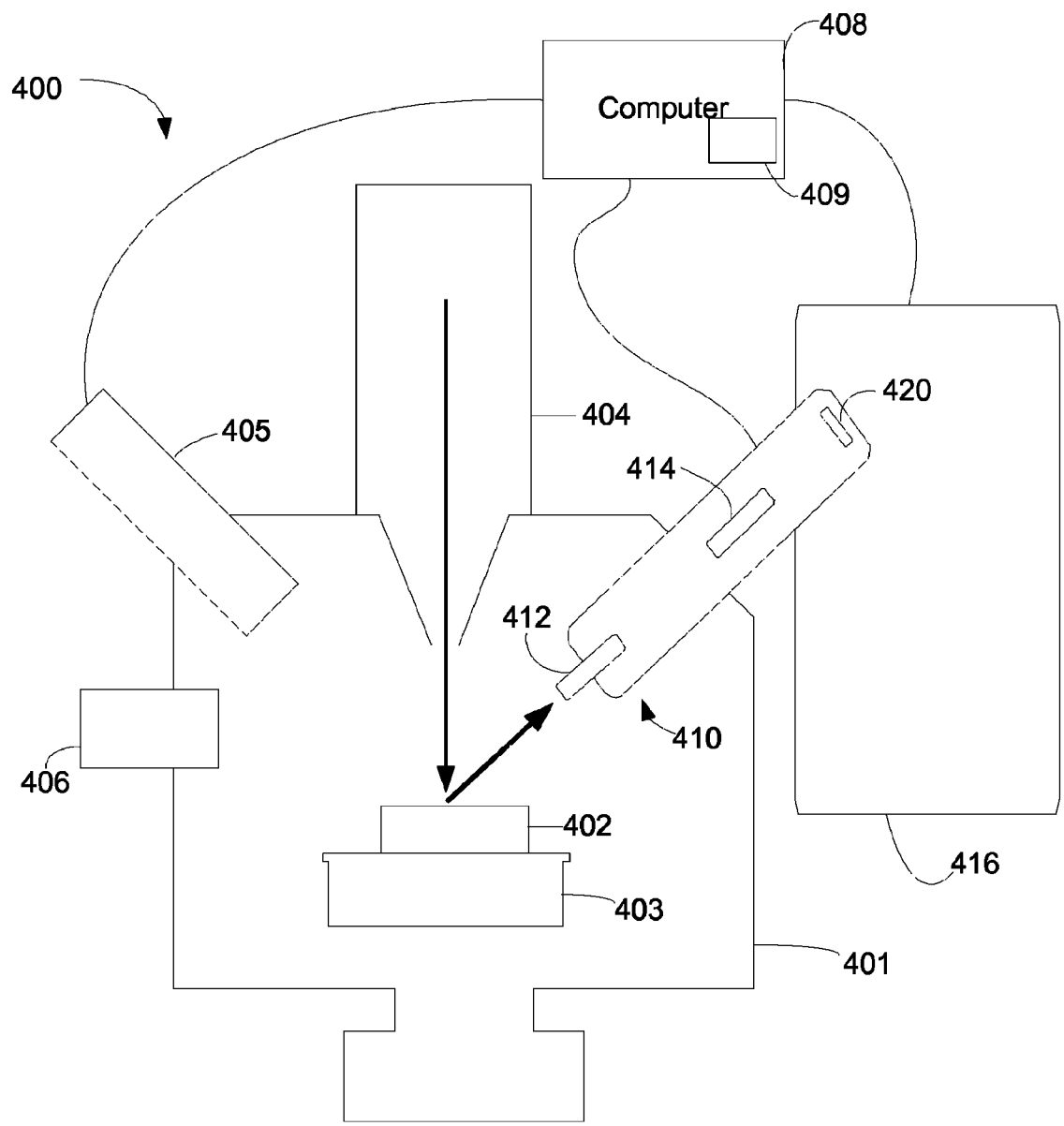
FIG. 4 shows a preferred embodiment of a microcalorimeter-type EDS system of the present invention.

A preferred embodiment of the invention comprises an x-ray microcalorimeter together with a dual beam system configured so as to enable high-resolution two-dimensional or three-dimensional x-ray mapping. FIG. 4 shows a preferred embodiment of the present invention. A microcalorimeter-type EDS system 400 includes a vacuum chamber 401 for maintaining a sample 402 on a sample XYZ stage 403, electron beam column 404 and an ion beam column 405. Electron beam column 404 includes a high brightness electron source, such as a Schottky emitter or cold field emitter, and ion column 405 is preferably includes a liquid metal ion source or a high brightness plasma source. A laser beam could be provided in place of or in addition to the focused ion beam system for removing material from the surface. The vacuum chamber could be a high vacuum chamber or the higher pressure vacuum chamber of an environmental scanning electron microscope. The system also preferably includes a plasma generator 406 for generating a plasma to remove contamination, such as carbon deposition, from the sample 402 before and during processing. A computer 408 controls the operation of the parts of system 400. A computer memory 409 stores a program for operating system 400 in accordance with the methods of the present invention.

An x-ray optic 410 has a large acceptance angle, preferably greater than 10 degrees, more preferably greater than 15 degrees, and most preferably about 20 degrees or greater. The acceptance angle is the greatest angle at which a ray entering the opening will be transmitted through the optic. That is, a ray entering the optic parallel to an axis of the optic will be transmitted, but a ray entering the optic at a sharp angle to the axis will not be transmitted. X-ray optic 410 is preferably of the glass capillary bundle type.

X-ray optic 410 preferably includes a point-to-parallel collimating lens 412 and then a parallel-to-point focusing lens 414 to transfers the x-rays from the vacuum chamber to detector assembly 420, which may include multiple individual detectors. The x-ray focusing optic can alternatively be comprised of a single point-to-point glass capillary focusing lens. A point-to-point focusing optic receives x-rays emanating from a point on the surface and focuses those x-rays to a point on the detector. Point-to-parallel-parallel-to-point optics receive x-rays from a point on the sample, collimate the x-rays so that they are moving parallel to each other for a distance, and then the parallel rays are converged back to a point. Point-to-parallel and parallel-to-point optical elements allow the x-rays to be routed over a range of distances between the sample to the detector simply by changing the distance between the elements 412 and 414, but the additional optical element also reduces the efficiency of the transfer.

The glass capillary bundle is similar to the one specified in U.S. Pat. No. 6,094,471 to Silver et al., but with an increased acceptance angle. Such x-ray optics are available commercially, for example, from X-Ray Optical Systems, Inc., East Greenbush, N.Y. The increased entrance angle allows the optic to receive x-rays from a larger solid angle from the sample. A gold foil-type optic can also be used, to reduce cost. The x-ray optic typically functions as a low pass filter and can be tuned to maximize the transmission of low energy x-rays, and to reject undesired higher energy x-rays. The x-ray optic preferably has a focal length of between 10 mm and 1000 mm, for example, 470 mm, and rejects x-rays above an energy of approximately 2.3 keV. The focal length is the distance from the sample to the x-ray optic. The rear focal length is the focal length from the optic to the focal plane that typically contains the detector that receives the x-rays. The front and rear focal lengths may be equal or different.

The microcalorimeter preferably provides a large solid angle of collection, that is, a solid collection angle greater than $10^{-3}$ sr, more preferably greater than $10^{-2}$ sr, and most preferably greater than $10^{-1}$ sr. The large solid angle can be achieved, for example, through the use of a high efficiency x-ray focusing optic or by detector placement in close proximity to the sample. The large solid angle allows more of the x-rays generated at the sample to be routed to the detector.

Figure 5:
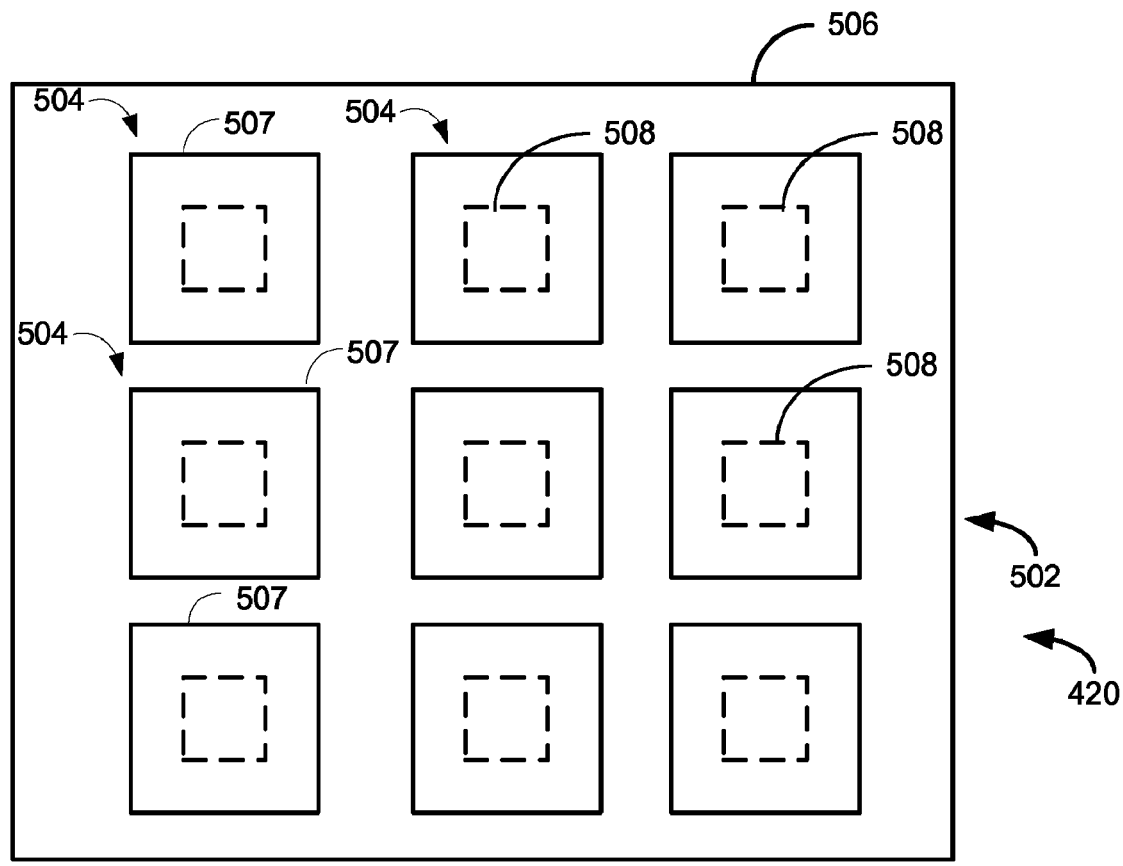
FIG. 5 shows an array of x-ray detectors.

Detector assembly 420 preferably includes multiple individual detectors cooled by a single cryostat. FIG. 5 shows a preferred detector assembly 420 comprises an array 502 that preferably includes at least nine individual detectors 504, all cooled by a single cryostat 506. Each includes an x-ray absorber 507 and a temperature sensor 508 between the absorber 507 and the cryostat 506, with the temperature sensor connected to the cold sink by the leads as in FIG. 6 below. Multiple individual detectors increase the count rate of the detector assembly by preventing pulse pileup artifacts. The x-rays from the sample are spread over multiple detectors, so that while one detector is temporarily unavailable due to its detecting a first pulse, other detectors can be detecting other incoming x-rays. The use of multiple detectors allows each individual detector to be designed for higher resolution without reducing the overall ability of the system to process incoming x-rays. That is, the thermal connection between the absorber and the cold sink can be weaker so that the signal from each pulse is greater, thereby providing higher energy resolution while reducing the maximum count rate requirement of the individual detector.

The x-ray flux is preferably the same at each of the multiple detectors comprising the detector array 502. Depending on the x-ray optics and the area of the array 502, the constant flux profile may be achieved by positioning the x-ray detector array 502 in the focal plane of x-ray optic 410, or x-ray detector array 502 may be positioned away from the focal plane so that the x-ray flux is decreased and the x-ray image expanded over the array.

Figure 6:
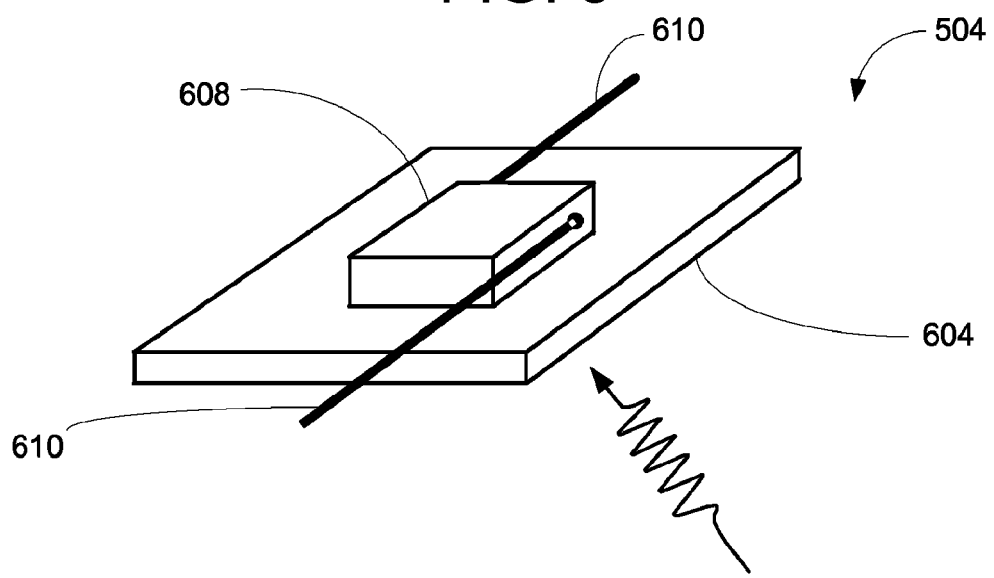
FIG. 6 shows an individual x-ray detector.

FIG. 6 shows a preferred individual x-ray detector 504 that comprises a tin absorber 604 maintained at about 60 mK and a temperature measuring device 608, which is in thermal contact but electrically isolated from absorber 604. The absorber 604 is preferably about 200×200 microns in area and about 10 microns thick. Temperature measuring device 608 preferably is preferably a germanium semiconductor, doped with Se, Ga and As by neutron transmutation doping. Neutron transmutation doping provides a very uniform doping profile with a dopant concentration greater than $10^{16}$ cm$^{-2}$. Leads 610 provide electrical and thermal links from the temperature sensor 606 to a pre-amplifier and a cold bath. The leads 610 from the multiple x-ray detectors are in contact with cryostat 506 to cool the absorbers back to operating temperature after detecting a pulse and warming. The thermal conductance between the tin absorber and the cold sink is preferably sufficiently high for the absorber to cool back to operating temperature in less than 300 μs. The detectors of FIG. 5 can provide an energy resolution of better than 3 eV at approximately 2 keV.

Figure 7:
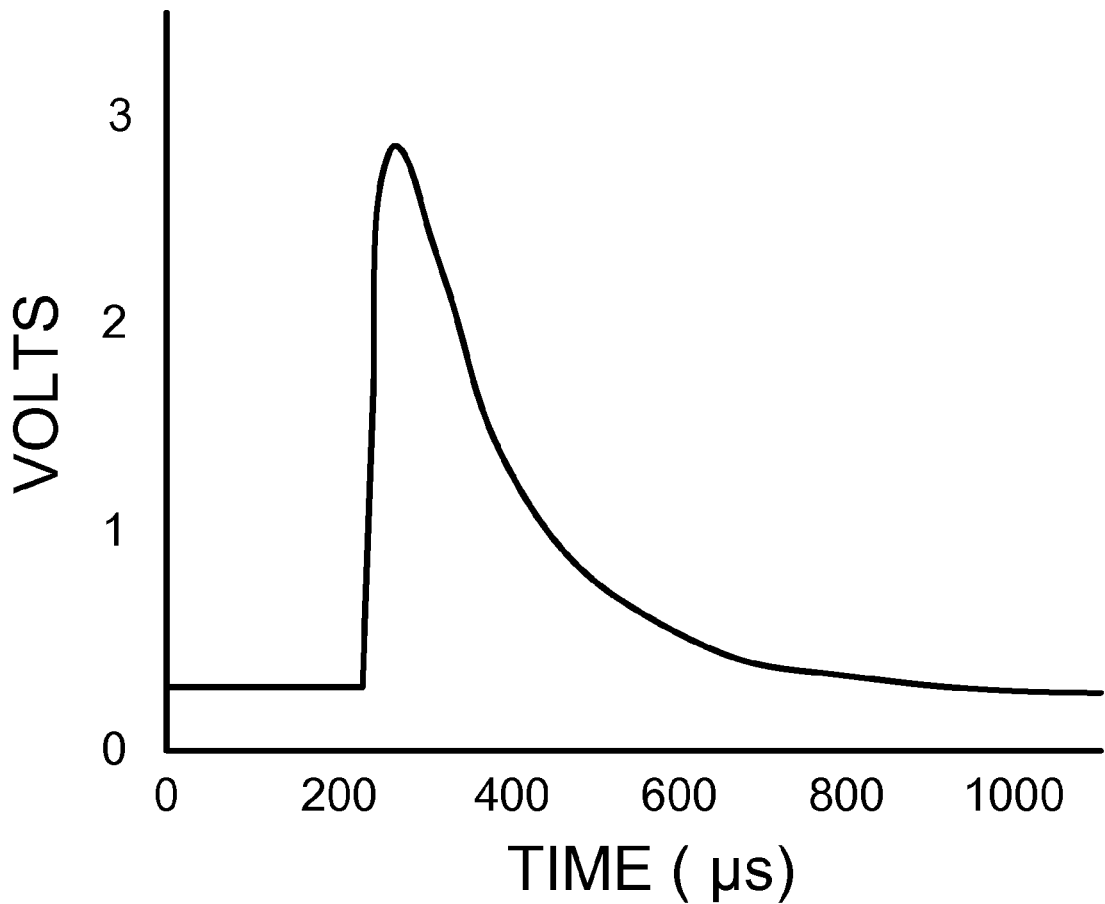
FIG. 7 shows a typical output pulse from a detector of FIG. 6

FIG. 7 shows a typical output pulse from a detector. The signal height is related to the ratio of the energy of the detected x-ray and the heat capacity of the detector. The pulse height can be increased by reducing the thermal conductivity between the absorber and the cold sink, but then the tail will extend further, reducing the number of counts possible per second. Reducing the size of the detector reduces its heat capacity, thereby increasing the signal height. Using multiple detectors allows each detector to be smaller, thereby increasing the signal height and improving resolution.

The size of the x-ray image in the focal plane of the x-ray optic will depend on the design and focal length of the optic. If the image is significantly smaller than the area occupied by the multiple sensors, then the sensors can be moved away from the focal plane until the x-ray image occupies most of the sensor array area. Because the x-ray image is typically circular and the detector array is not, as the image is further defocused and becomes larger, some of the x-rays will impact outside of the detector array. Skilled persons will be able to determine an optimum position for the detector array so that the x-rays are sufficiently spread among the detectors to provide a high pulse count rate, while minimizing x-rays that fall outside the detector area.

The output of the multiple detectors are preferably multiplexed into a single JFET pre-amplifier, as described in U.S. Pat. No. 6,310,350.

A preferred dual beam can optionally employ:
A cryogenic specimen stage to enable the analysis of vitrified biological samples, and other vacuum-incompatible materials.
High speed electron beam scanning and electron imaging to enable real time drift compensation during high resolution x-ray mapping. The electron beam scan rate is defined relative to the inverse of the x-ray map acquisition time. A fast scan rate is preferably 10 times greater than the inverse of the map acquisition time, more preferably 100 times greater, and more preferably still 1000 times greater. For example it the x-ray map acquisition time is 10 minutes, then the frame time is preferably 60 s, more preferably, 6 sec, and most preferably shorter than 0.6 sec.

Various embodiments may include:
High speed electron beam scanning and periodic RF plasma cleaning of the sample (e.g., a 20 sec plasma clean once every 5 min) to minimize contamination buildup during low energy, high resolution mapping. Gases that can be used for plasma cleaning include air, $H_2O$, $O_2$ and $H_2$.
An electron flood gun to minimize charging during low energy x-ray analysis and during sample milling by positive ions.
The injection of gases such as $H_2O$ and $O_2$ into the specimen chamber during x-ray mapping in order to minimize contamination buildup and charging. The gases are preferably injected in small quantities using a capillary-style gas injection system.
A heating stage to gently heat the sample (e.g., up to 50, 100 or 150° C.) in order to minimize contamination buildup during x-ray mapping.
Gas-assisted etching to maximize the sample surface quality during 3 dimensional analysis.

Besides using the ion beam to successively expose layers for three-dimensional X-ray mapping, the ion beam can also be used to expose buried sample features for X-ray analysis. Embodiments of the invention can also be used for high resolution imaging of stained biological tissue, and tissue labeled with functionalized x-ray tags. Such imaging modes can optionally be applied to thin bio samples, and combined with in-situ scanning transmission electron microscopy (STEM) imaging in order to achieve correlative microscopy. Optimal correlative microscopy will likely be achieved by performing x-ray mapping using a low beam energy (e.g., 1.5 to 5 keV, in order to maximize the x-ray fluorescence efficiency of nano-scale tags and thin bio tissue) and STEM using an elevated beam energy (e.g., 10 to 30 keV). Embodiments of the invention include the use materials that are optimal for x-ray tags—i.e., materials, such as Mg, Al and Si that exhibit a good compromise between stopping power and efficient, characteristic, low energy x-ray emission lines. Specifically, analyses using low energy K lines are preferred over L lines and L lines are preferred over M lines; however, the stopping power of materials with low energy K lines is typically lower than that of materials with low energy L & M lines, so a skilled person can determine single and multi-element materials that are expected to be optimal as a function of beam energy and tag diameter, for example, by using Monte Carlo simulations.

Embodiments of the invention enable three-dimensional, high resolution x-ray mapping. Three-dimensional, high resolution x-ray mapping has different system requirements compared to conventional EDS mapping because conventional EDS mapping is typically performed at low magnifications, using high electron beam energies. Prior art microcalorimetry-based x-ray mapping is limited by shot noise due to very low count rates.

Applicants have developed a system to characterize a microcalorimeter-type EDS system using a "figure of merit" (FOM) that can be determined for various systems. The figure of merit represents the x-ray count in each peak per unit charge injected into the sample by the electron beam. The figure of merit therefore has units of x-ray counts per nano Coulomb (nC$^{-1}$). The figure of merit of a particular system will depend on the x-ray fluorescence efficiency, x-ray absorption rate inside the sample, and on the efficiency of the collection and detection system. That is, a detector that detects x-rays over a larger solid angle will have a higher figure of merit. Applicants have determined that a figure of merit of at least 100 nC$^{-1}$ is preferred for characteristic x-rays emitted from a major constituent of the sample volume interrogated by the electron beam, in order for the EDS system to provide a sufficient signal to form an x-ray map with an acceptable signal-to-noise ratio in a reasonable period of time, for example, less than about 20 minutes. In many cases, a system having a figure of merit of less than 100 nC$^{-1}$ would require too large of a beam current to yield a sufficient x-ray signal-to-noise ratio in a reasonable time.

After defining the acceptable limits on some parameters such as the minimum useful map size, maximum acceptable beam current and the maximum acceptable acquisition time, one can determined the count rate corresponding to a particular FOM (i.e., a particular signal-to-noise ratio) and therefore determine the number of detectors required to process the detected x-rays. In a particular system, the collection efficiency is fixed and the count rate can be increased by increasing the beam current. Alternatively, one can fix the beam current and increase the acquisition time to increase the total number of counts without increasing the count rate. The figure of merit is a single quantity that can be used to quantify the effectiveness of a microcalorimeter x-ray detector at x-ray mapping, and to quantify the corresponding x-ray count rate at a given beam current.

The minimum preferred figure of merit of 100 nC$^{-1}$ derives from the assumption that an x-ray map should include at least 100 pixels by 100 pixels, the beam current should be smaller than or equal to 1 nA and map acquisition should not take longer than 16.7 minutes to perform. Using the figure of merit approach, applicants have been able to create embodiments of the invention that provide unexpected improvements over the prior art and are practical for two-dimensional or three-dimensional x-ray mapping with high spatial resolution, and with maps having 100 pixels by 100 pixels, or more.

The figure of merit is defined as (N*X)/(I*T), in which:
"N" is the minimum number of pixels needed to form an x-ray map (e.g., 100×100)
"X" is the minimum number of x-ray counts per pixel in a single x-ray peak (e.g., 10, corresponding to a shot noise-limited signal-to-noise ratio of $10^{0.5}$~3.2)
"I" is the maximum acceptable beam current (e.g., 1 nA)
"T" is the maximum acceptable map acquisition time (e.g., 10 to 20 minutes)

For example, an x-ray map of 100 pixels by 100 pixels providing 10 counts per pixel in an x-ray peak that is obtained using a beam current of 1 nA over a time period of 16.7 minutes provides a figure of merit of 100 nC$^{-1}$ and a shot noise-limited signal-to-noise ratio of approximately 3.2.

The FOM can be scaled arbitrarily by relaxing or tightening the above data collection parameters. However, the above values are defined to represent the limits that are preferably met or exceeded to enable practical high spatial resolution x-ray mapping.

The FOM is a function of the maximum acceptable map acquisition time (T) and, at a given electron beam current, the FOM translates to a specific x-ray count rate, and hence defines the number of detectors needed to avoid pulse pileup artifacts. For example, the above values of N, X, I and T yield a count rate of 100 cps per x-ray peak. In a real-world example, an x-ray spectrum may contain, for example, 5 peaks, and a high quality microcalorimeter may have an FOM of 1000 nC$^{-1}$ at each peak, translating to an x-ray arrival rate of 5000 cps at the detector array when using an electron beam current of 1 nA. Hence, if the maximum count rate of a single detector is, for example, 500 cps, then an array of more than 10 detectors is needed to avoid pulse pileup artifacts (i.e., 500 cps per detector plus additional detectors needed to process x-rays comprising the Bremsstrahlung background radiation).

Table I shows the effect of electron beam current and count rate on map acquisition times corresponding to a figure of merit of 100 nC$^{-1}$.

TABLE 1

| Current (nA) | Counts/sec (CPS) | Time per Pixel (sec) | Time per line (min) | Time per map (min) |
|---|---|---|---|---|
| 0.01 | 1 | 10 | 16.67 | 1666.67 |
| 0.1 | 10 | 1 | 1.67 | 166.67 |
| 1 | 100 | 0.1 | .17 | 16.67 |
| 10 | 1000 | 0.01 | .02 | 1.37 |
| 100 | 10000 | 0.001 | 0.00 | .017 |

The mapping times for some configurations in Table 1 are impractically long, and the count rates for others would require a large number of detectors to avoid pulse pileup artifacts. As the electron beam current increases from 0.01 nA to 100 nA, more x-ray photons are generated per unit time by the electron beam and delivered to the sample. If the detector were capable of the count rates in the second column, the third through fifth column describes the times required per pixel, per 100 pixel line, and per 100×100 pixel map. Applicants have determined that less than 20 minutes is an acceptable time in many cases to determine a 100×100 pixel map, and a count rate of 100 counts per second is achievable at 1 nA, as described in the third row of the Table 1.

Figure 8:
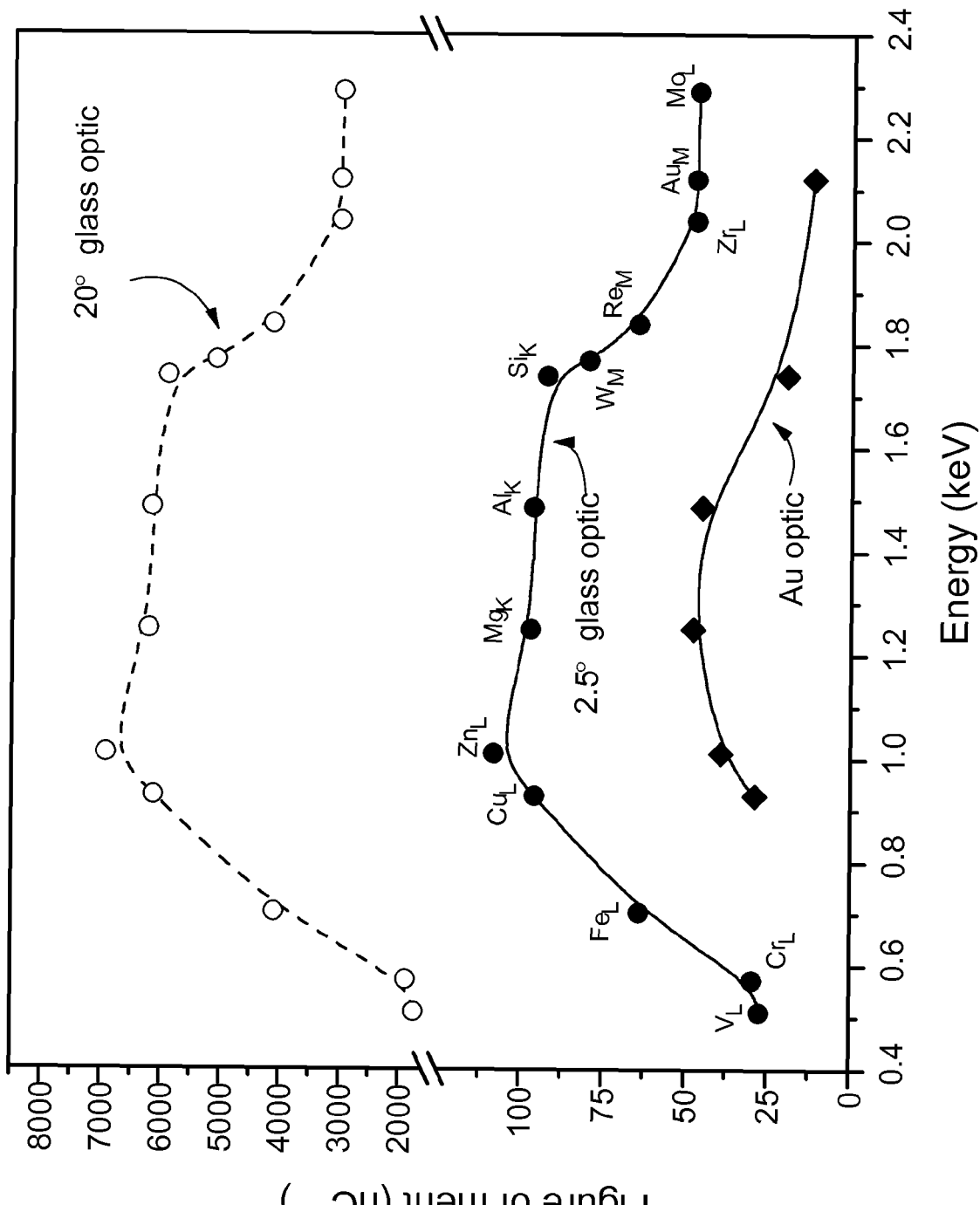
FIG. 8 shows the figure of merit for a number of characteristic x-ray peaks excited in single element materials by a 5 keV electron beam.

Because the figure of merit depends on the collection efficiency, it will vary with the efficiency of the x-ray optic that collects x-rays from the sample and transmits them to the detector. FIG. 8 illustrates the figure of merit for a number of characteristic x-ray peaks excited in single element materials by a 5 keV electron beam, corresponding to:

"Au optic": This curve is representative of prior art microcalorimeters that utilize Au spiral x-ray focusing optics. Such systems are appropriate for spectroscopy, but the throughput is inadequate for x-ray mapping (since the figure of merit is smaller than 100 nC$^{-1}$ for each x-ray line shown in the plot).

"2.5° glass optic": This curve is representative of typical prior art microcalorimeters that utilize glass capillary x-ray focusing optics with small opening angles. Such systems are appropriate for spectroscopy, and the throughput is only just adequate for x-ray mapping using some of the x-ray lines (since the figure of merit is greater than 100 nC$^{-1}$ for some of the x-ray lines shown in the plot, e.g., the Zn L line). However, the throughput is adequate only for mapping the distributions of major constituents, and completely inadequate for some emissions (e.g., the Au M emission). More importantly, the throughput is inadequate for x-ray mapping using electron beam energies smaller than 5 keV because the FOM decreases as the electron beam energy is decreased below 5 keV.

"20° glass optic": This curve is representative of an embodiment in the invention that utilizes a glass capillary x-ray focusing optic with a large opening angle of 20°. Such a system is appropriate for high resolution x-ray mapping since the figure of merit is much greater than 100 nC$^{-1}$ for all x-ray lines shown in the plot. In addition, the throughput is adequate for x-ray mapping using electron beam energies smaller than 5 keV (e.g., if the beam energy is reduced from 5 to 2.5 keV, the FOM corresponding to the Cu L emission decreases by approximately a factor of 4.5, yield an FOM that's still much greater than 100 nC$^{-1}$).

Figure 9:
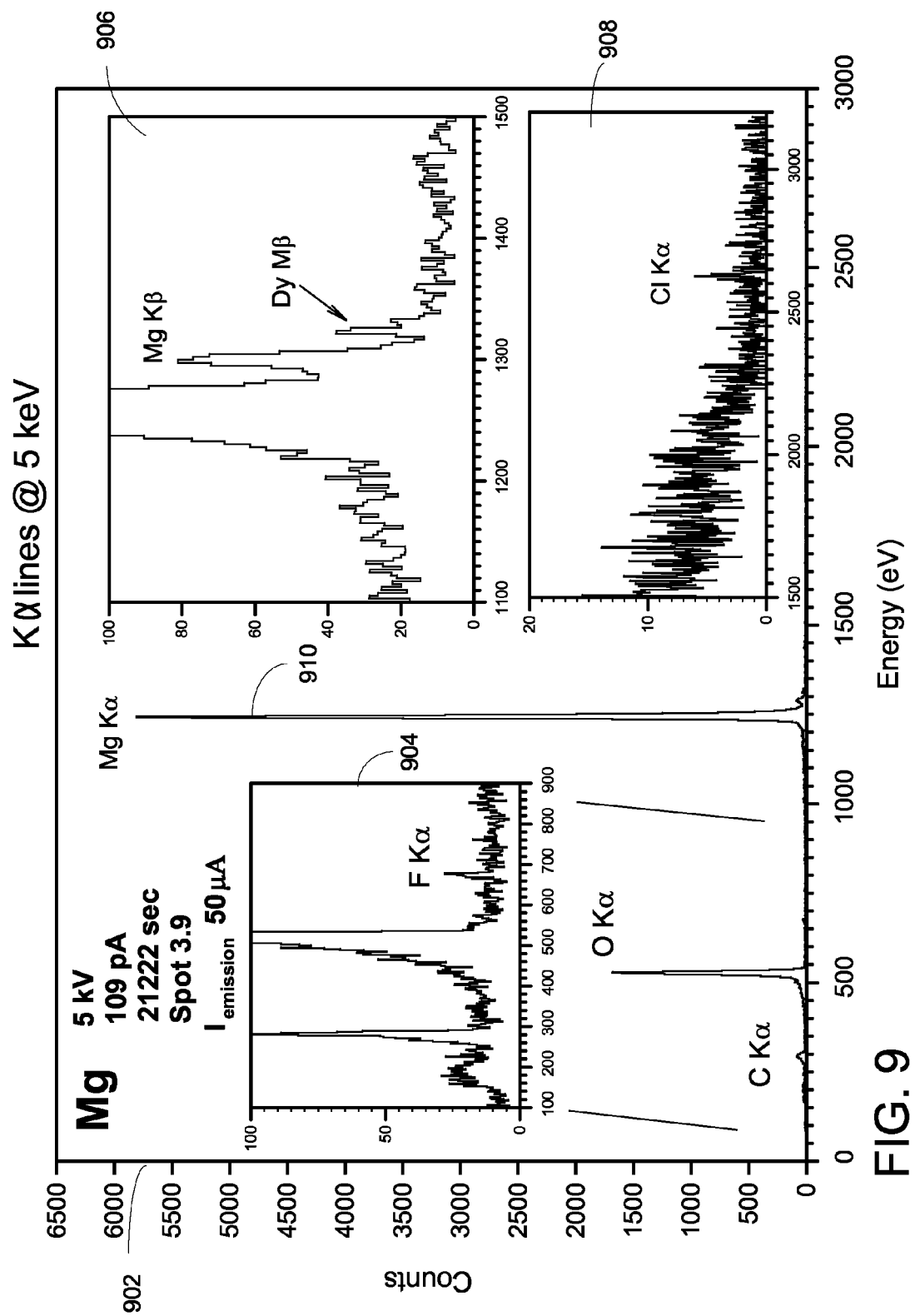
FIG. 9 shows an x-ray spectrum, with portions of the spectrum shown in enlarged views.

FIG. 9 shows an overall graph 902 of an x-ray spectrum, and smaller graphs 904, 906, and 908 showing enlarged portions of graph 902. When a typical prior art system is used, the Mg Kα peak, designated by reference number 910 has a figure of merit of 12.9 nC$^{-1}$. When an improved glass capillary with a wider acceptance angle, the figure of merit improves to 387 $nC^{-1}$ and when the glass capillary with a 20° opening angle is used, the figure of merit increases to 7367 $nC^{-1}$, which corresponds to a count rate of 764 cps when using an electron beam current of 100 pA. Such a count rate can be processed by two or three detectors. If the current were to be increased to 1 nA, the count rate would increase to 7640 cps, and additional detectors would be required to avoid pulse pileup. Similarly, if there are 10 x-ray lines of equal intensity, then a count rate of 7640 cps would need to be accommodated at a beam current of 100 pA.

Similarly, the Oxygen Kα peak from the native oxide overlayer has a figure of merit of 3.7 $nC^{-1}$ for a typical prior art system, 111 $nC^{-1}$ for a system using an improved glass capillary with a wider acceptance angle, and 2190 $nC^{-1}$ for a system using an improved glass capillary with a 20° acceptance angle.

Preferred embodiments of the invention provide a figure of merit for the Au M line emitted from bulk Au irradiated by 5 keV electrons of greater than 100 $nC^{-1}$, and more preferably provide a figure of merit greater than 1000 $nC^{-1}$. Some embodiments provide a figure of merit for the Mg K line of bulk Mg (containing a native oxide) irradiated by 5 keV electrons greater than 500 $nC^{-1}$, and more preferably provide a figure of merit greater than 1000 $nC^{-1}$.

Figure 10:
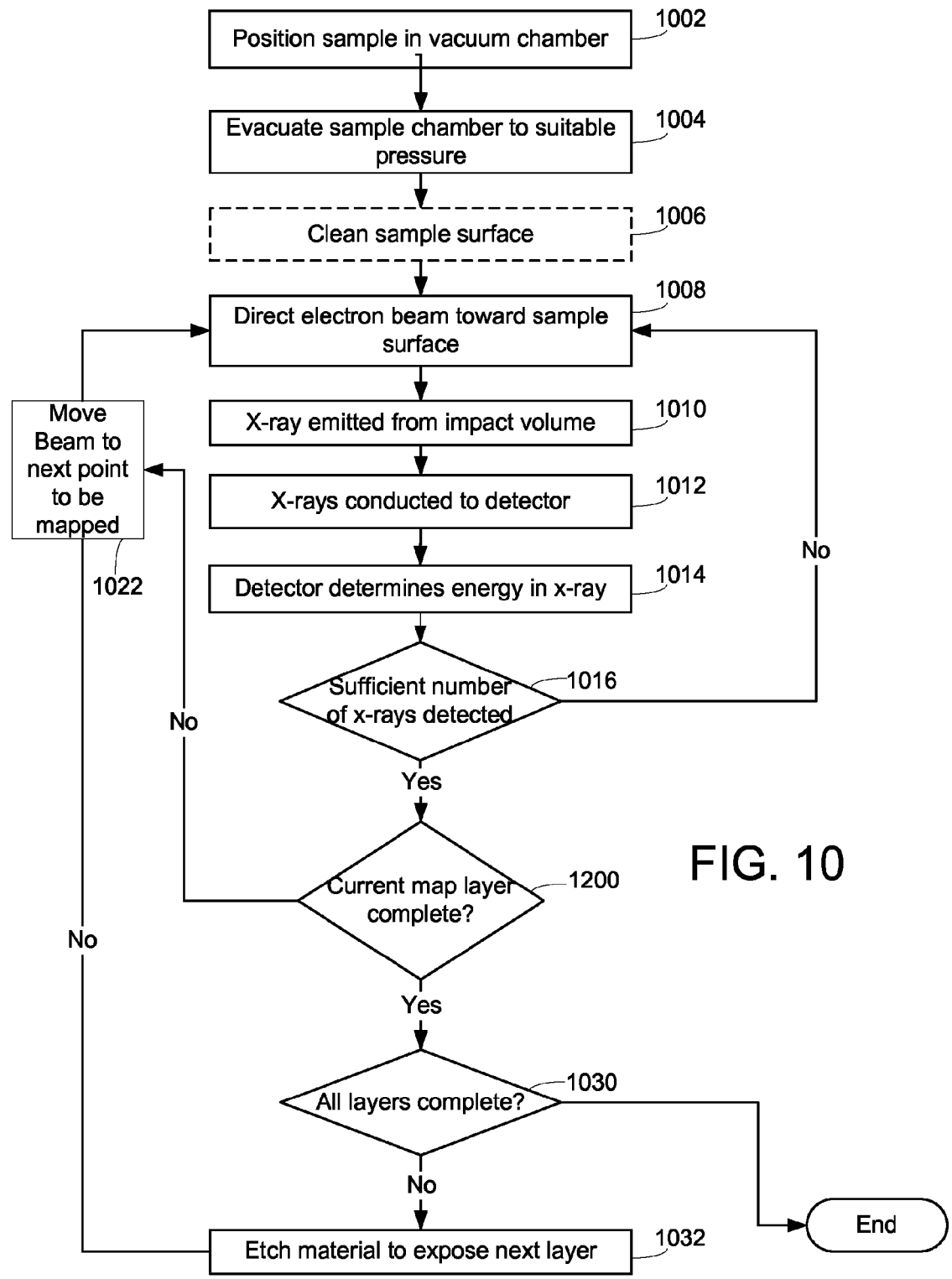
FIG. 10 shows a preferred method of three-dimensional x-ray mapping in accordance with the invention.

FIG. 10 shows a preferred method in accordance with the present invention. In step 1002 a sample is positioned in the vacuum chamber of a dual beam system with a microcalorimeter-type EDS of the present invention. The sample may be, for example, a semiconductor circuit or a biological sample. In step 1004, the sample chamber is evacuated to a suitable pressure, depending on the sample. In optional step 1006, an ion beam or a plasma is directed toward the surface of the sample to clean the surface. In step 1008, an electron beam is directed toward a point on the substrate surface. For x-ray mapping, the beam preferably has an energy of between 2000 eV and 7000 eV, typically about 4,000 eV or less and a beam current of between 0.01 nA and 2 nA, typically 0.5 nA. The beam preferably has a spot size of less than 30 nm and more preferably less than 15 nm, and even more preferably 10 nm or less. As the electrons impact the surface, x-rays are emitted from the point in step 1010.

In step 1012, the x-rays are conducted by an x-ray optic from the sample surface and from the optic to x-ray detectors. In step 1014, the detectors determine the energies of the x-rays received while the electron beam is at the first point. Decision block 1016 determines when a predetermined dwell period has passed or when a sufficient number of x-rays have been detected to determine the material present at the first point at a sufficient signal-to-noise ratio. The electron beam remains directed to the same point for a predetermined dwell time, which is sufficient to determine the composition of the point to a desired accuracy. The dwell time required at each point will depend on the electron beam current and the type of material. Preferably, the electron beam is positioned at each point for a sufficient time so that at least ten counts are registered for each x-ray peak present. In some embodiments, the electron beam remains directed to each point for about 0.1 seconds. In some embodiments, dwell time varies at different points on the sample surface until a pre-determined number of x-rays is detected, and the dwell time at each point is recorded and used to normalize the number of x-rays detected from each point. When sufficient data is received to map the current point, if the map is not complete and additional points are to be mapped (decision block 1020), the electron beam moves to the next point in step 1022 and the detection process is repeated from step 1008. In one embodiment, the electron beam scans an area of at least 100 dwell points by 100 dwell points to form a map with 10,000 pixels. During mapping the position of the electron beam is optionally recalibrated periodically, for example, by viewing a fiducial, to compensate for drift in the electron beam position. When an entire array of pixels is completed, it is determined in decision block 1030 whether there is an additional layer to be mapped. If so, the ion beam removes a layer of material in step 1032. For example, the ion beam may remove about 20 nm The ion beam may be used with a precursor gas to assist etching or may simply sputter material. Skilled persons can readily determine the required ion beam parameters for removing a layer. In step 1022, the process of mapping the new layer begins again with step 1008.

In another embodiment of the invention, the electron beam is scanned rapidly and repeatedly over the sample region of interest. The data collection system records the energy of each x-ray detected by the microcalorimeter, as well as the electron beam position at the sample surface. Alternatively, the data collection system records the energy of each x-ray and the time at which each x-ray is detected. The time information is then used to calculate the electron beam position corresponding to each x-ray detection event and to construct an x-ray map. The x-ray map can either be constructed in real time, during analysis, or after data collection is complete. The fast scanning method has the advantage that a large number of electron images can be collected during x-ray detection. This is possible because the emission rate of electrons is typically much greater than the emission rate of x-rays from the sample. Common secondary and backscattered electron detectors such as the Everhart-Thornley scintillator-photomultiplier detector and the Si solid state detector can be used for electron imaging. If the sample is sufficiently thin, transmitted electrons can also be used to form electron images. The electron images can be used to recalibrate the electron beam position periodically to correct for sample or beam drift occurring during x-ray mapping.

The multi-detector array can be placed into or outside the focal plane of the optic so as to maximize the x-ray collection efficiency and minimize the maximum x-ray flux incident onto any single detector. The dual beam system provides an electron beam (for low energy, high resolution x-ray mapping) and a means to remove surface material from the sample (to enable depth-resolved x-ray analysis). Material removal is preferably performed by a focused ion beam, but can also be achieved using a broad ion source, a plasma source, or a laser.

The invention has broad applicability and can provide many benefits as described and shown in the examples above. The embodiments will vary greatly depending upon the specific application, and not every embodiment will provide all of the benefits and meet all of the objectives that are achievable by the invention.

Although much of the previous description is directed at semiconductor wafers, the invention could be applied to any suitable sample. Further, whenever the terms "automatic" "automated" or similar terms are used herein, those terms will be understood to include manual initiation of the automatic or automated process or step. In the following discussion and in the claims, the terms "including" and "comprising" are used in an open-ended fashion, and thus should be interpreted to mean "including, but not limited to . . . " The accompanying drawings are intended to aid in understanding the present invention and, unless otherwise indicated, are not drawn to scale.

Although the present invention and its advantages have been described in detail, it should be understood that various changes, substitutions and alterations can be made to the embodiments described herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

We claim as follows:

1. A system for x-ray mapping, comprising:
   an ion beam focusing column;
   an electron focusing column for focusing an electron beam into a sufficiently small spot to resolve material separated by 15 nm;
   an x-ray optic for receiving x-rays emitted from the sample, the x-ray optic receiving and transmitting x-rays impinging on the optic entrance at angles up to at least 10 degrees; and
   multiple x-ray detectors, each x-ray detector including:
      an absorber for absorbing x-rays exiting the x-ray optic; and
      a temperature sensing device for converting a change in temperature of the x-ray absorber into an electronic signal, the multiple x-ray detectors capable of resolving energy difference of 15 eV,
   the system capable of determining a material map composed of 100 pixels by 100 pixels while collecting x-rays for a period of less than twenty minutes.

2. The system of claim 1 in which the x-ray optic receives and transmits x-rays impinging on the optic entrance at angles up to at least 15 degrees.

3. The system of claim 1 in which the multiple x-ray detectors comprise at least nine x-ray detectors.

4. The system of claim 1 in which the x-ray optic comprises a bundle of capillaries.

5. The system of claim 1 in which the temperature sensing device includes a neutron transmutation doped germanium semiconductor.

6. The system of claim 1 further comprising one or more computers for controlling the system, the computers including memory computer storing a program for directing the ion beam focusing column to remove a layer of material from a portion of the sample, scanning the electron beam over at least a part of the portion of the sample, and recording the material present at different locations on multiple layers of the sample, the material being determined by information from the x-ray detectors.

7. The system of claim 1 in which the system is characterized by a figure of merit of greater than 500 $nC^{-1}$ for the Mg K line of bulk Mg containing a native oxide irradiated by 5 keV electrons.

8. The system of claim 1 in which the system is capable of producing a signal to noise ratio of less than 4 for the Au M line emitted from bulk Au irradiated by 5 keV electrons.

9. A method of forming a high spatial resolution, high energy resolution x-ray map of a sample, comprising:

a. directing a beam of electrons having energies of less than 5,000 eV toward a sample in a vacuum chamber, the electron beam forming a spot having a diameter of less than 50 nm on the sample;
   b. conducting x-rays created by the impact of the electrons on the sample through an x-ray optic towards multiple cryogenic x-ray detectors;
   c. determining the energy of the x-rays impacting the detector to determine the material present at the location at which the electron beam impacts the sample;
   d. moving the impact point of the electron beam to a different point on the surface and repeating steps b and c for an array of at least 5,000 points in a time period of less than one hour to produce a map of material present in the region scanned by the electron beam.

10. The method of claim 9 further comprising removing a layer of material including the points to which the electron beam was directed and repeating steps a-d for a second array of points below the first array of points to produce a three-dimensional x-ray map.

11. The method of claim 10 in which removing a layer of material includes directing a focused ion beam toward the sample to remove the layer of material without removing the sample from the vacuum chamber.

12. The method of claim 9 in which conducting x-rays created by the impact of the electrons on the sample through an x-ray optic towards multiple cryogenic x-ray detectors includes conducting x-rays using a bundle of capillaries, the bundle having an acceptance angle of greater than 10 degrees.

13. The method of claim 9 in which determining the energy of the x-rays impacting the detector includes measuring the increase in temperature of an x-ray absorber using a neutron transmutation doped germanium crystal.

14. The method of claim 9 in which moving the impact point of the electron beam to a different point on the surface and repeating steps b and c includes moving the impact point of the electron beam to an array of at least 10,000 points in a time period of less than one half hour to produce a map of material present in the region scanned by the electron beam.

15. The method of claim 9 conducting x-rays created by the impact of the electrons on the sample through an x-ray optic towards multiple cryogenic x-ray detectors includes focusing the x-rays onto multiple detectors.

16. The method of claim 9 conducting x-rays created by the impact of the electrons on the sample through an x-ray optic towards multiple cryogenic x-ray detectors includes defocusing the x-rays to spread them over multiple detectors.

17. A system for x-ray mapping of a sample to show the material present at different positions on the sample, comprising:
   an electron focusing column capable of focusing an electron beam to a sufficiently small beam spot to resolve material separated by 15 nm;
   an x-ray optic for receiving x-rays emitted from the sample, the entrance to the x-ray optic receiving x-rays over a solid angle of at least 10 degrees; and
   multiple x-ray detectors, each x-ray detector including:
      an absorber for absorbing x-rays exiting the x-ray optic; and
      a temperature sensing device for converting a change in temperature of the x-ray absorber into an electronic signal, the multiple x-ray detectors are capable of resolving energy difference of 15 eV,
   the system capable of determining a material map composed of 100 by 100 pixels while collecting x-rays for a period of less than twenty minutes.

18. The system of claim 17 in which the multiple x-ray detectors comprise at least nine x-ray detectors.

19. The system of claim 17 in which the temperature sensing device includes a neutron transmutation doped germanium semiconductor.

20. The system of claim 17 further comprising one or more computers for controlling the system, the computers including memory computer storing a program for directing the ion beam focusing column to remove a layer of material from a portion of the sample, scanning the electron beam over at least a part of the portion of the sample, and recording the material present at different locations on multiple layers of the sample, the material being determined by information from the x-ray detectors.

21. The system of claim 17 in which the system is characterized by a figure of merit of greater than $1000 \text{ nC}^{-1}$ for the Au M line emitted from bulk Au irradiated by 5 keV electrons.

* * * * *

UNITED STATES PATENT AND TRADEMARK OFFICE
CERTIFICATE OF CORRECTION

PATENT NO. : 8,357,894 B2
APPLICATION NO. : 12/853998
DATED : January 22, 2013
INVENTOR(S) : Toth et al.

It is certified that error appears in the above-identified patent and that said Letters Patent is hereby corrected as shown below:

In the Specification:

Column 1, Line 42 – Please change "result of the" to read --result of--;

Column 2, Line 7 – Please change "shows at" to read --shows a--;

Column 5, Line 29 – Please change "Many the aspects" to read --Many aspects--;

Column 5, Line 41 – Please change "405 is preferably" to read --405 preferably--;

Column 5, Line 65 – Please change "transfers the" to read --transfer the--;

Column 6, Line 39 – Please change "single cryostat." to read --single cryostat 416.--;

Column 7, Line 7 – Please change "preferably is preferably" to read --is preferably--;

Column 7, Line 60 – Please change "example it the" to read --example the--;

Column 7, Lines 61/62 – Please change "60 s" to read --60 sec--;

Column 9, Line 65 – Please change "Table I" to read --Table 1--;

Column 10, Line 23 – Please change "the Table 1" to read --Table 1--;

Column 11, Line 65 – Please change "block 1020" to read --block 1200--.

Signed and Sealed this
Thirtieth Day of July, 2013

Teresa Stanek Rea
*Acting Director of the United States Patent and Trademark Office*